United States Patent [19]
Dimeff

[11] Patent Number: 4,583,406
[45] Date of Patent: Apr. 22, 1986

[54] SIGNAL PROCESSOR

[75] Inventor: John Dimeff, San Jose, Calif.

[73] Assignee: Mark Telephone Products, Inc., Santa Clara, Calif.

[21] Appl. No.: 615,194

[22] Filed: May 30, 1984

[51] Int. Cl.⁴ ............................................. G01N 29/04
[52] U.S. Cl. .................................. 73/59 L; 73/40.5 A
[58] Field of Search ................... 73/59 L, 40.5 A, 602, 73/658

[56] References Cited

U.S. PATENT DOCUMENTS 3,192,516  6/1965  Simpkins et al. .................. 73/59 L
3,222,635 12/1965  Simpkins et al. .................. 73/59 L
3,308,424  3/1967  Simpkins et al. ................ 73/40.5 A Primary Examiner—Anthony V. Ciarlante
Attorney, Agent, or Firm—Townsend and Townsend

[57] ABSTRACT

Apparatus for processing a composite noise signal containing sonic and ultrasonic components generally in a frequency range of about 20 Hz–100 KHz to make audible both components of the signal includes a heterodyne circuit operable in response to a rectangular wave local oscillator signal to produce output signals which are within the frequency range of human hearing.

21 Claims, 4 Drawing Figures

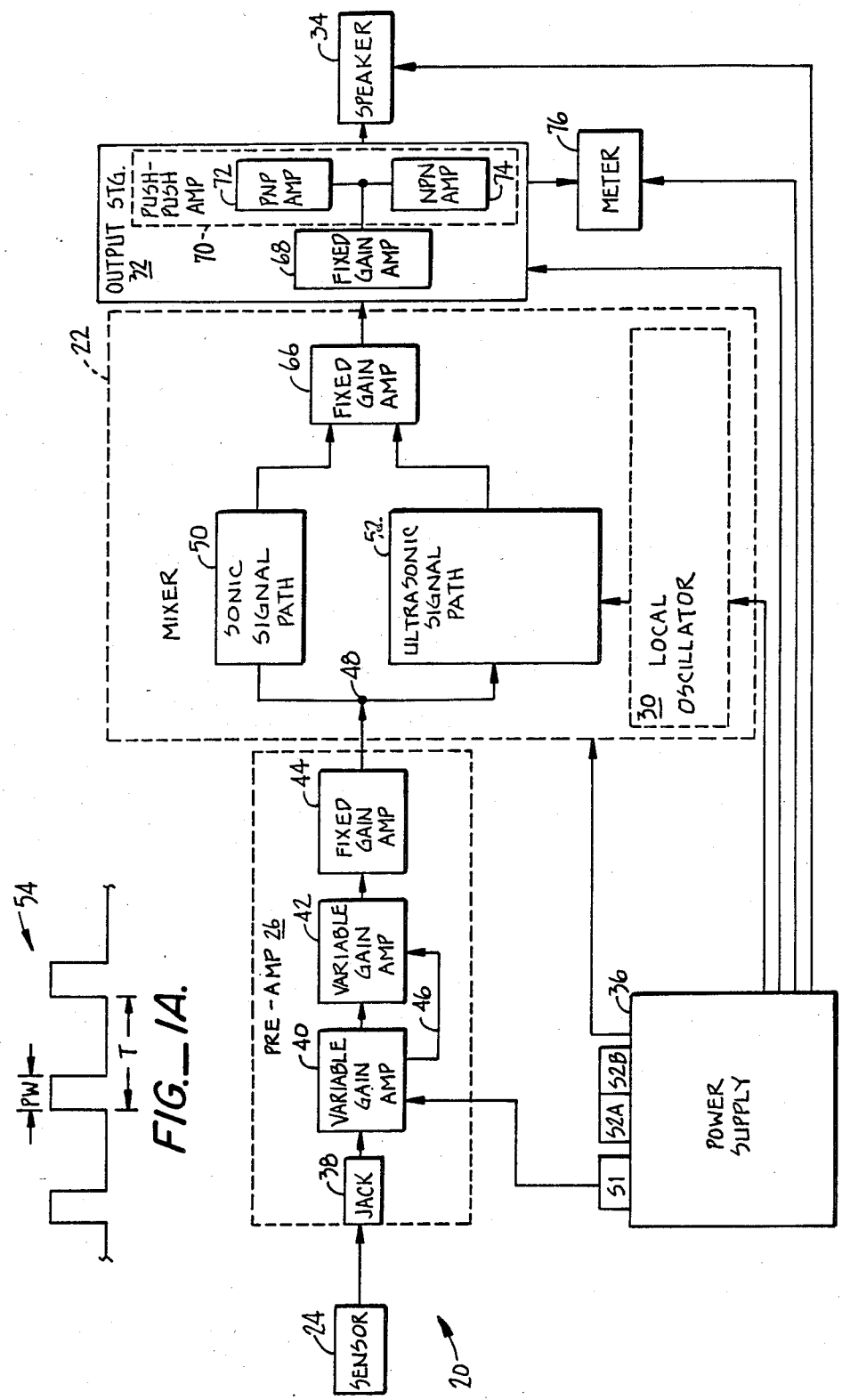

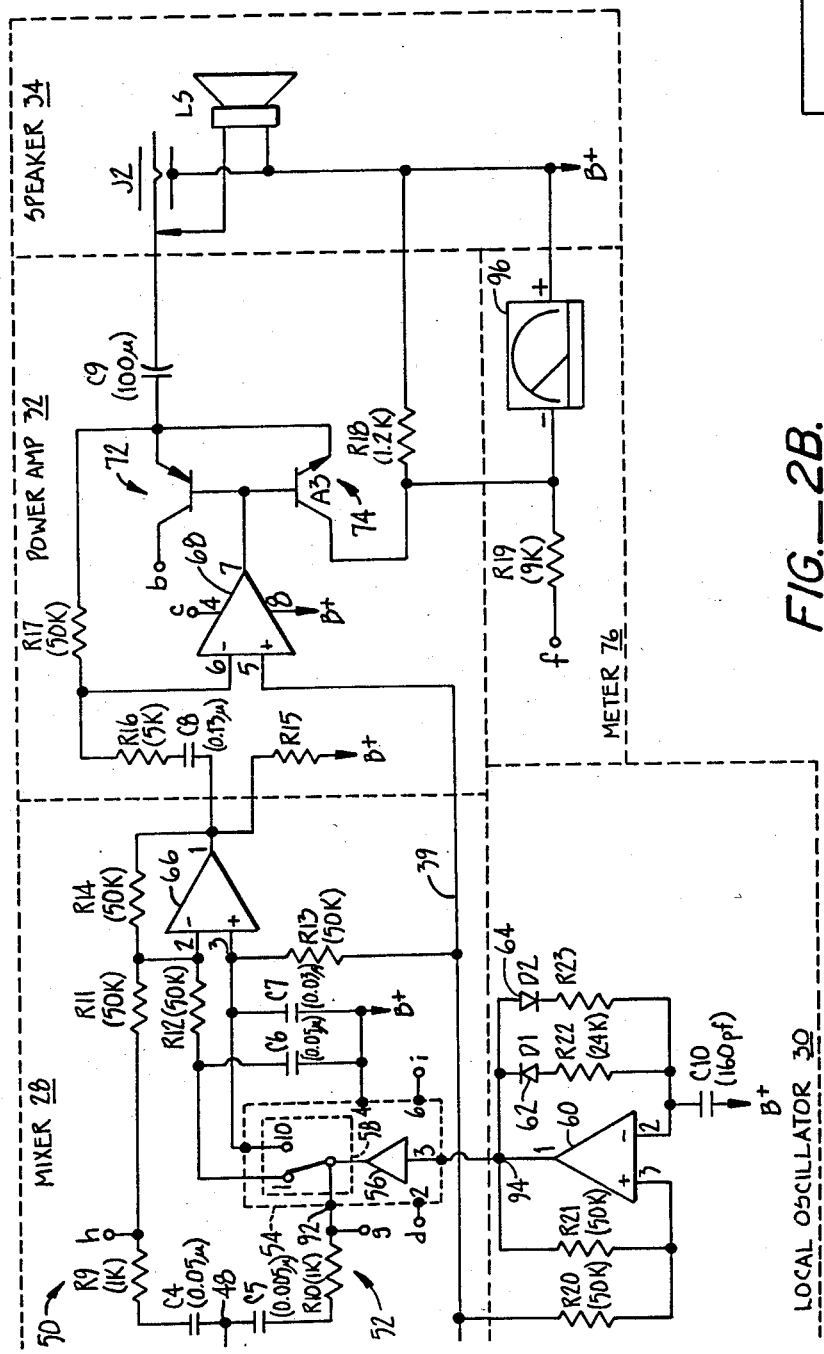

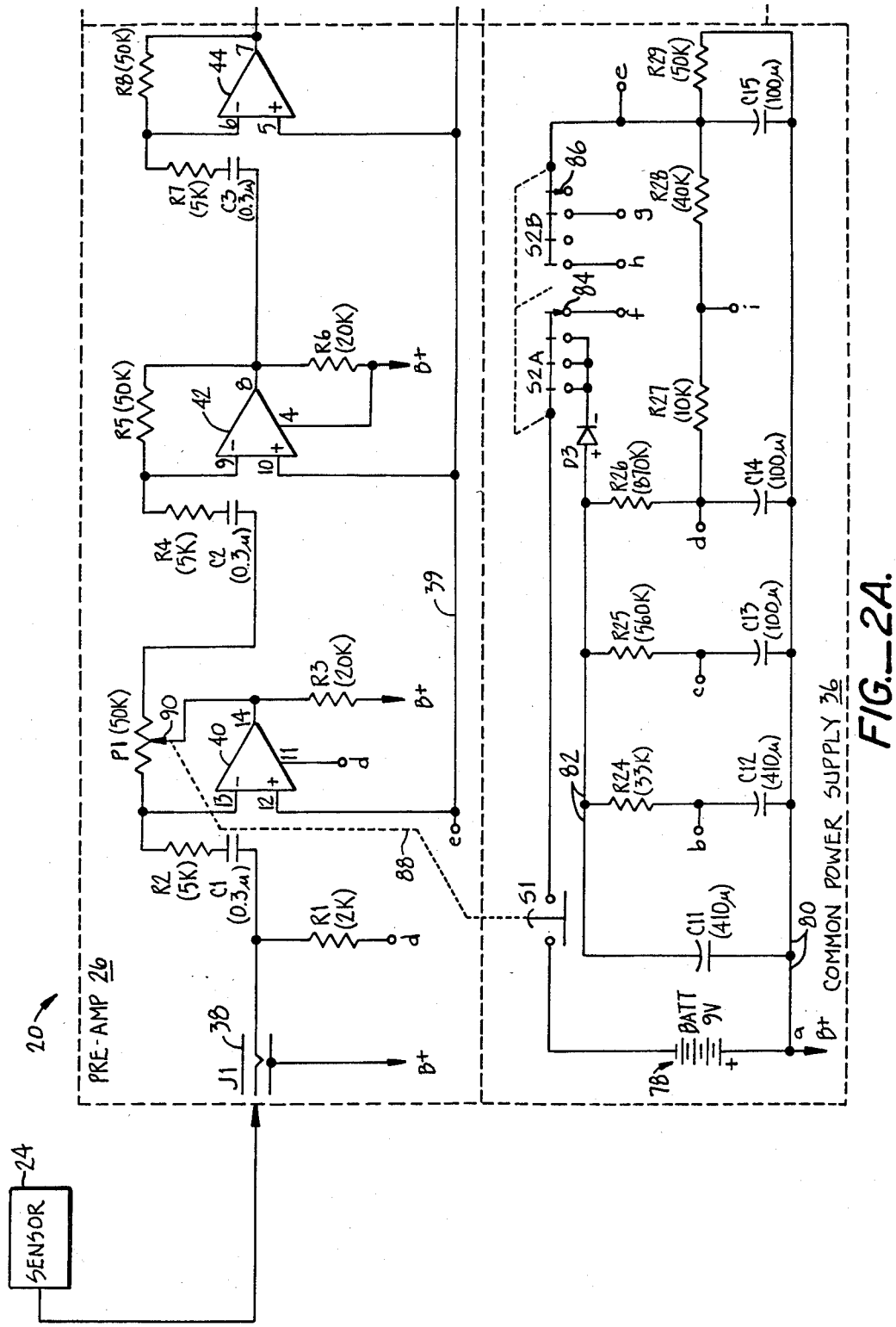
FIG.—2A.

SIGNAL PROCESSOR

The field of this invention relates generally to electronic signal processors, and more particularly to a signal processor capable of processing both the sonic and ultrasonic components of signals to produce resultant output signals which are within the frequency range of human hearing.

BACKGROUND OF THE INVENTION

In the telecommunications cable industry, it has been found that system performance is improved by air pressurizing bundles of telephone wires housed within a sealed sheath tube, typically in the form of a tough plastic material. Unfortunately, the sheath can be perforated, allowing the pressurized air to rush out through the perforation and permitting ingress of water, dirt and the like. The out-rushing air generates a composite signal having sonic or ultrasonic frequency components, and sometimes both. To locate these perforations or leaks, remote sensing devices and associated electronics capable of responding to the leak generated noise have been developed.

Present techniques involve inserting an acoustically sensitive device along the sheath tube path and measuring the length of rod required to position the device adjacent to the leak. The device is typically sensitive to either (1) the sonic components or (2) some pre-selected narrow band of the ultrasonic component (e.g., 36–44 KHz) of noise vibrations generated by the air escaping through the perforation. According to these techniques, the vibration sensitive device, usually an acoustic sensor, is mounted on a flexible feeding apparatus and introduced into and along a length of the sheath tube. The sensor is electrically coupled to a metering device having a visual display which responds to output signals produced by the sensor when detection of a noise-emitting perforation is made. The distance of insertion of the sensor determines the location of the perforation.

It has been found, and believed heretofore unknown, that sheath tube perforations are capable of generating noise-emitting frequencies throughout the entire range of 0–100 KHz. Large perforations tend to generate noise vibrations having primarily a sonic frequency content; smaller perforations generate ultrasonic frequencies up to about 100 KHz. Thus, a disadvantage of either of the above approaches is that they fail to cover the full range of frequencies capable of being generated by noise-emitting perforations, i.e., 0–100 KHz.

SUMMARY OF THE INVENTION

The present invention provides an audible and/or visual response to the full range of frequencies capable of being generated by the composite noise or vibrations produced by the outrush of air through a perforation.

According to the present invention, therefore, there is provided apparatus for receiving the sonic and ultrasonic vibrations produced by a perforation in a pressurized length of sheath tube of the type described above, and producing therefrom an indication of the presence of either or both vibration components. The invention includes (1) a receiver stage, including a pre-amplifier, for converting the vibrations to electrical signals and amplifying those electrical signals; (2) a heterodyne or mixer stage, including a local oscillator, operable in the ultrasonic range of interest (i.e., 15 KHz–100 KHz); and (3) an output stage that performs a 15 KHz low-pass filtering function. Perforation-produced vibrations having a frequency component generally in the audible range, i.e., 20 Hz–15 KHz, are amplified and passed directly to the converter to produce an audible indication. Vibrations having frequency components greater than 15 KHz, i.e., in the frequency range of 15 KHz–100 KHz, are applied to the heterodyne stage to produce a difference frequency in the audible range of approximately 20 Hz–15 KHz. The resultant difference frequencies are then applied to the converter stage to also produce an audible indication.

In the preferred embodiment, the local oscillator circuit produces local oscillator signal, $f_{lo}$, in the form of a rectangular wave having a fundamental frequency of 30 KHz. The ratio of the pulse width to the period of the rectangular wave is set to approximately 1:3, thereby producing a local oscillator signal rich in the second and third harmonics of the fundamental frequency. Thus, when heterodyned with $f_{lo}$, the received ultrasonic signals, $f_{in}$ in the 15 KHz–100 KHz range, produce a heterodyned signal resultant containing sum and difference frequencies $f_{lo} \pm f_{in}$. The heterodyned signal applied to the output stage which acts, in part, as a low pass filter passing only the 20 Hz–15 KHz signal components to a speaker system to produce an audible response.

The preferred embodiment of the present invention employs a solid-state switch to perform the heterodyne operation. The solid-state switch is operated by the local oscillator to switch the incoming ultrasonic signal between the positive and negative inputs of a differential amplifier. The output of the differential amplifier provides the heterodyned signal.

BRIEF DESCRIPTION OF THE DRAWINGS

FIG. 1 is a block diagram of a signal processor according to this invention;

FIG. 1A is a simplified representation of the square wave signal produced by the local oscillator of the processor shown in FIG. 1; and FIGS. 2A and 2B together show a detailed circuit diagram of the signal processor of FIG. 1.

DETAILED DESCRIPTION OF A PREFERRED EMBODIMENT

System Overview

Referring first to FIG. 1, a signal processor, designated generally with the reference numeral 20, is broadly shown as including a sensor 24, a pre-amplifier 26, a heterodyne (mixer) circuit 22, including a local oscillator 30, and an output stage 32.

The sensor 24 is typically in the form of a conventionally available acoustic vibration crystal, and is adapted to be inserted adjacent to a telephone wire bundle enclosed within an air-pressurized tubular sheath (not shown). As sensor 24 approaches a perforation in the sheath, it will receive the sonic and/or ultrasonic noise vibrations generated by the air as it rushes from the interior of the tube out through the perforation. In response the sensor 24 will generate electrical signals corresponding to the vibrations that have a frequency content in either the sonic or ultrasonic range i.e., generally in the 20 Hz–100 KHz range.

Sensor 24 is coupled to deliver the generated electrical signals to a pre-amplifier 26 for amplification. The amplified signal is then communicated to a heterodyne or mixer stage 22. The mixer stage 22 heterodynes the electrical signals received from the preamplifier 26 with the local oscillator signal, $f_{lo}$, produced by local oscillator 30, to produce the sum and the difference of the frequencies of the original signals. The sum and difference frequency signals are delivered to a power amplifier 32 where, after amplification, they are applied to a speaker 34. Speaker 34 performs two functions: First, it acts as a 15 KHz low pass filter, passing only those difference frequencies of the signals in the 150 Hz–15 KHz range (in reality, frequencies from 0–150 Hz are ignored); second, it converts the electrical signals to corresponding sonic signals which are heard by the human operator.

A power supply 36 is coupled to provide voltage and current as necessary to the preamplifier 26, mixer 22, local oscillator 30, power amplifier 32 and speaker 34.

Detailed Discussion

More particularly stated, FIG. 1 shows in greater detail the features of signal processor 20.

Sonic and ultrasonic noise vibrations received by sensor 24 are converted to electrical signals and conducted to the preamplifier 26 through an input jack 38. From here the sensor produced signals travel for successive amplification through an amplifier 40 and an amplifier 42, both of which have variable gain, and on to another amplifier 44 whose gain is fixed.

Power supply 36 is coupled through a switch S1 to preamplifier 26 at amplifier 40. As indicated by a line 46, amplifier 40 is coupled to amplifier 42 in such a manner that an adjustment of the gain of amplifier 40 also adjusts the gain of amplifier 42.

Additionally, power supply 36 is connected to deliver power to preamplifier 26, mixer 22, local oscillator 30, power amplifier 32.

The amplified signals emerging from amplifier 44 leave preamplifier 26 and are conducted to mixer 22 at junction 48. The sonic components of the amplified signal (i.e., the frequency signals within the range of from 0 to 15 KHz) are routed through a sonic signal path 50; the ultrasonic components of the amplified signal are routed through an ultrasonic signal path 52 which, as will be seen, includes circuitry for heterodyning the amplified signals with that produced by the local oscillator 30.

As indicated above, the local oscillator 30 produces a square wave signal having a pulse repetition frequency (PRF) of approximately 30 KHz. The square wave pulse train, illustrated in FIG. 1A and designated generally with the reference numeral 54, is shown as having a pulse width (PW) and a period (T). A rectangular wave signal whose fundamental frequency is 1/T can be the source of a number of periodic harmonic signals whose frequencies are N/T, the amplitudes of which are related to the ratio of the square wave's pulse width to its period. In the present invention, the preferred ratio of the pulse width PW to the period T of the square wave 54 is approximately 1:3. This will produce second and third (that is, N=2 and N=3) harmonic signal amplitudes comparable to that of the fundamental frequency (30 KHz). Thus, the affect of producing square wave 54 as described is that the local oscillator 30 provides three periodic signals of interest: A 30 KHz fundamental frequency signal, a 60 KHz second harmonic signal, and a 90 KHz third harmonic signal.

The local oscillator signal ($f_{lo}$) is heterodyned with the incoming sonic and ultrasonic signals, producing sum and difference frequencies. As will be noted below, the particular heterodyne scheme used herein modulates the ultrasonic signals, but causes the sonic signals to be averaged about zero. Accordingly, the sonic signals are passed to a fixed gain amplifier 66 only by the sonic signal path 50 and not the ultrasonic signal path 52. The ultrasonic signal path heterodynes the incoming ultrasonic signals, producing sum and difference frequencies that are applied to the fixed gain amplifier 66.

The amplified sonic and ultrasonic signals are conducted from the fixed gain amplifier 66 to the power amplifier 32, comprising a fixed gain amplifier 68 and a push-pull amplifier 70, and from there to speaker 34 where both sonic and the heterodyned ultrasonic signals (i.e., the difference frequencies produced by the heterodyne operation) below 15 KHz are converted to audible responses by the speaker.

Having described the basic implementation and function of the invention, with reference to FIGS. 1 and 1A, a closer look at the heterodyning operation can now be taken. In essence, the invention functions to shift or "fold" signals appearing in the ultrasonic range of 15 KHz–100 KHz into the sonic range (0–15 KHz) of frequencies. For example, assume for the moment that the sensor 24 detects noise vibrations having a 25 KHz component. If passed by the sonic signal path 50 alone, amplified and applied to speaker 34, no audible response would be heard by those with normal hearing. On the other hand, when heterodyned and passed to the fixed gain amplifier 66, the ultrasonic signal path 52, sum frequencies of 55 KHz (30 KHz+25 KHz), 85 KHz (60 KHz+25 KHz), etc., and difference frequencies of 5 KHz (30 KHz−25 KHz), 35 KHz (60 KHz−25 KHz), etc. are applied to the output stage 32 and speaker 34. Functioning as a 15 KHz low pass filter, only the 5 KHz component is ultimately produced as an audible indication of the detected noise vibrations by the output stage 32 and speaker 34. In similar fashion, noise vibrations having frequency components, for example, of 40, 75, and 100 KHz will, when heterodyned with the 30, 60, and 90 KHz harmonic components of the local oscillator signal and will produce corresponding audible responses at speaker 34 of 10, 15, and 10 KHz. In effect then, each of the 30, 60 and 90 KHz frequencies becomes a "local oscillator" frequency against which the frequency of the ultrasonic signal is heterodyned, producing the difference frequencies that are in the 0–15 KHz.

Detailed Description: Circuit Diagram

Turning now to FIGS. 2A and 2B, the detailed schematic diagram of the present invention is illustrated. Turning first to the power supply 36, there is included a pair of switches S2A and S2B that are switchable between a number of discreet positions, as indicated by associated respective arrows 84 and 86. Switch S2A, in addition to being connectable to a diode D3, can be switched to connect a pin "f" of power supply 36 to other components of system 20 as shown. Likewise, switch S2B can be switched through a pin "h" and a pin "g" to connect filter capacitor C15 to other components of system 20 as shown in FIGS. 2A and 2B.

Switches S2A/S2B function to select and deselect the signal paths used to communicate the signal from preamplifiers 26 to the output stage 32 (via the fixed gain amplifier 66). For example, when switched so that the wiper 86 connects to point h, the sonic signals to the fixed gain amplifier 66 are by-passed to B+ via filter capacitor C15. The ultrasonic path 52 is unaffected so that the ultrasonic components of any detected noise vibrations will be passed, in heterodyned form, to the amplifier 66. Alternatively, if the wiper 86 is connected to pin g, the ultrasonic signals are bypassed to B+, and the sonic signals are passed to amplifier 66. Any other position of the wiper 86 of switch S2B allows both the sonic and ultrasonic signal paths 50 and 52 to function normally.

This aspect of the invention allows the operator to select between audible response to the sonic or ultrasonic components of the detected noise vibrations, to the exclusion of the other, or to include both. This provides the operator with the capability of determining whether the perforation is large (and, therefore, producing noise vibrations having substantial sonic components) or small (containing mostly ultrasonic components).

Power supply 36 is provided with a switch S1 activating power supply 36 to provide power to system 20. Additionally, the shaft of S1 is used for adjusting the gain of preamplifier 26 as indicated by a dashed line 88. Specifically, switch S1 is connected to adjust the resistance of a potentiometer P1 (i.e., S1 and P1 are "ganged"). The gain of amplifier 40 and 42 are simultaneously changed by adjustment of potentiometer P1.

Note that pins "a-g" connect to corresponding pins "a-g" distributed throughout the components of system 20 shown in FIGS. 2A and 2B. As can be seen, some pins in power supply 36 connect with more than one component having corresponding pins in system 20. For example, power supply 36 pin d connects to preamplifier 26 at two locations as shown (i.e., to a resistor R1 and also to amplifier 40), as well as to mixer 28 at one location as shown (i.e., to a pin 2). Pin a connects to supply the main supply voltage, B+. Pins b-d and i connect to supply bias and/or other voltages (i.e., other than B+) to the signal processor 20.

As shown in FIG. 2B, the sonic path 50 includes a series arrangement of a capacitor C4, a resistor R9, and a resistor R11, terminating at the inverting-input of amplifier 66. The ultrasonic path 52 is shown as including, in series, a capacitor C5, a resistor R10, and a solid-state switch 54, including an input junction 92. Input junction 92 connects to a switching element 58 (schematically illustrated as a two-position switch) within switch 54.

The electrical signal from preamplifier 26 (FIG. 2A) is applied to the solid-state switch 54 where it is alternately switched between output pins 1 and 10 of the solid-state switch 58. When applied to pin 1, the signal passes through resistor R12 into the inverting (−) input of amplifier 66. When applied to pin 10, the signal passes directly through to the non-inverting (+) input of amplifier 66. Switching the incoming (from preamplifier 26) ultrasonic signal between the inverting and non-inverting inputs of amplifier 66 functions to modulate the signal by the local oscillator signal to produce the desired heterodyning action.

Solid-state switch 54 includes a chopper amplifier 56 (model type DG387 manufactured by Siliconix Corporation of California) the output of which is connected to drive the switching element 58 to cause it to alternately connect input junction 92 to output pins 1 and 10. The input to chopper amplifier 56 is coupled to local oscillator 30 through pin 94, to thereby receive the local oscillator signal $f_{lo}$.

Still referring to FIG. 2B, local oscillator 30 is shown as including a parallel arrangement of resistors, diodes and a capacitor, which are connected with difference amplifier 60 to junction 94 for providing an input signal to pin 3 of 54.

The output of amplifier 60 is fed back, via a resistor R21, to its non-inverting (+) input. Power supply 36 is coupled through B+ and a capacitor C10 to the negative input of amplifier 60. A reverse diode pair D1, D2 are respectively connected through a resistor R22 (with a value range of 20K-25K, and preferably 24K) and a resistor R23 of value below about 10K but preferably not below about 5K to the inverting input of amplifier 60. So constructed, oscillator 30 generates the 30 KHz square wave signal that drives the solid-state switch 54.

The output of amplifier 66 is coupled to the inverting (−) input of amplifier 68 through a series capacitor C8 and resistor R16. The output of amplifier 68 is coupled to the interconnected base leads of an NPN transistor amplifier 74 and a PNP transistor 72. The collector lead of transistor 72 is connected through a pin b to the respective pin b within power supply 36 (FIG. 2A) for obtaining proper bias. The emitter lead of transistor 74 is coupled to the emitter lead of lead transistor 72. So connected, transistors 72 and 74 form a push-pull amplifier that drive the speaker 34 from its interconnected emitter leads, which interconnection is coupled, through a capacitor C9, to the speaker 34.

Power amplifier 32, through capacitor C9, is connected to speaker 34 in a manner that provides an output signal through a jack J2 designed for receiving a plug from headphones worn by a human operator.

The above specific embodiment is one of many possible constructions which achieve operation according to this invention. The above best mode is a necessarily narrow example, provided to illustrate the best mode of assembly and operation contemplated by the inventor at the time. It is by the appended claims that the breadth of the invention is established.

What is claimed is:

1. A signal processor, comprising:
    means for receiving a composite signal having sonic and ultrasonic frequency components;
    means for generating a local oscillator signal recurring at a selected fundamental frequency and containing significant signal components of a plurality of harmonics of said fundamental frequency signal;
    heterodyning means coupled to the receiving means and to the local oscillator frequency generating means for receiving the composite signal and the local oscillator signal, and for producing therefrom a difference signal indicative of the difference between any ultrasonic component of the composite signal and the local oscillator frequency signal; and
    output means coupled to receive the difference signal to produce therefrom an aural indication of the difference signal.

2. The signal processor of claim 1, wherein the generating means produces a 30 KHz fundamental frequency signal and a 60 KHz harmonic of the fundamental frequency signal.

3. The signal processor of claim 2, wherein the 30 KHz fundamental frequency signal is a rectangular wave signal.

4. The signal processor of claim 3, wherein the 30 KHz fundamental frequency signal has a pulse width to period ratio of approximately 3:1.

5. The apparatus of claim 1, the generating means further including a local oscillator circuit for producing the fundamental and harmonic frequency signals, comprising an amplifier connected in parallel to a series-connected first resistor and first diode, and in parallel with a series-connected second resistor and second diode, with the respective diodes connected in opposite directions.

6. The signal processor of claim 1, wherein the heterodyning means includes amplifier means having an inverting input and a non-inverting input, and including means intercoupling the receiving means to the amplifier means and operable in response to the local oscillator signal to alternately apply the composite signal to the inverting and the non-inverting inputs of the amplifier means.

7. The signal processor of claim 6, wherein the intercoupling means includes a solid-state switch.

8. The signal processor of claim 1, and wherein the heterodyning means includes a sonic signal path for communicating the sonic frequency component of the composite signal to the output means.

9. The signal processor of claim 1, wherein the heterodyning means includes a first signal path for communicating the sonic component of the composite signal to the output means and a second signal path that includes means for receiving the ultrasonic component of the composite signal, developing therefrom the difference signal, and communicating the difference signal to the output means.

10. The signal processor of claim 9, wherein the heterodyning means includes amplifier means having first and second inputs respectively coupled to the first signal path and the second signal path.

11. The signal processor of claim 10, wherein the second signal path includes means operable in response to the local oscillator signal for alternately coupling the ultrasonic component to the first and second inputs of the amplifier means.

12. The signal processor of claim 10, including means for selectively inhibiting communication of the sonic or the ultrasonic components of the composite signals to the output means.

13. The signal processor of claim 11, wherein the local oscillator signal is a rectangular wave having a pulse recurrence frequency of approximately 30 KHz.

14. The signal processor of claim 13, wherein the rectangular wave has a predetermined pulse width and a predetermined period sufficient to provide a fundamental periodic frequency, second harmonic periodic frequency, and third harmonic periodic frequency of approximately 30 KHz, 60 KHz, and 90 KHz, respectively.

15. The apparatus of claim 1, and wherein the output means includes speaker means coupled to receive the difference signal to produce the audible response therefrom.

16. A signal processor for producing an audible response to receipt of a composite signal having a sonic frequency component, an ultrasonic component, or both, the signal processor comprising:
    input means coupled to receive the composite signal;
    first circuit means for producing a local oscillator signal consisting of a fundamental frequency and signal components of a plurality of harmonics of the fundamental frequency;
    second circuit means coupled to the input means to receive the composite signal, and operable in response to the local oscillator signal for producing difference frequency signals from ultrasonic components of the composite signal in the frequency range of 15 KHz–100 KHz, the difference frequency signals being in the range of 0–15 KHz; and
    third circuit means coupled to the second circuit means for converting the difference signal to said audible response.

17. The signal processor of claim 16, wherein the local oscillator signal is a periodic rectangular wave having a pulse recurrence frequency of 30 KHz and a pulse width to period ratio of 1:3.

18. The signal processor of claim 16, wherein the local oscillator signal includes a fundamental frequency of approximately 30 KHz, a second harmonic signal of approximately 60 KHz, and a third harmonic signal of approximately 90 KHz.

19. The signal processor of claim 16, wherein the second circuit means includes a first circuit path for communicating the sonic component of the composite signal to the third circuit means, including means for developing said difference frequency, for communicating the composite signal to the third circuit means as the difference signal.

20. The signal processor of claim 19, including means for selectively communicating the sonic component of the composite signal or the difference signal to the third circuit means to the exclusion of the other.

21. The signal processor of claim 16, wherein the second circuit means includes difference amplifier means having a first input coupled to receive the at least the sonic component of the composite signal and a second input, and means coupled to receive the composite signal and operable in response to the local oscillator signal to alternately apply the composite signal to the first and second inputs of the difference amplifier means.

* * * * *